United States Patent
Yigal et al.

(10) Patent No.: US 11,202,858 B2
(45) Date of Patent: Dec. 21, 2021

(54) VERTICAL ASSEMBLY OF PCB

(71) Applicant: West Pharma. Services IL, Ltd., Ra'anana (IL)

(72) Inventors: Gil Yigal, Gan Yavne (IL); Yossi Bar-El, Beit Arye (IL)

(73) Assignee: West Pharma. Services IL, Ltd., Ra'anana (IL)

( * ) Notice: Subject to any disclaimer, the term of this patent is extended or adjusted under 35 U.S.C. 154(b) by 0 days.

(21) Appl. No.: 16/618,258

(22) PCT Filed: May 30, 2018

(86) PCT No.: PCT/US2018/035107
§ 371 (c)(1),
(2) Date: Nov. 29, 2019

(87) PCT Pub. No.: WO2018/222697
PCT Pub. Date: Dec. 6, 2018

(65) Prior Publication Data
US 2020/0405949 A1     Dec. 31, 2020

Related U.S. Application Data

(60) Provisional application No. 62/512,496, filed on May 30, 2017.

(51) Int. Cl.
*A61M 5/142* (2006.01)
*A61M 5/172* (2006.01)
*A61M 5/46* (2006.01)

(52) U.S. Cl.
CPC ........ *A61M 5/14248* (2013.01); *A61M 5/172* (2013.01); *A61M 5/46* (2013.01);
(Continued)

(58) Field of Classification Search
CPC .... A61M 5/15248; A61M 2005/14252; A61M 2005/1585; A61M 2205/3306
See application file for complete search history.

(56) References Cited

U.S. PATENT DOCUMENTS

2007/0104596 A1* 5/2007 Preuthun ........... A61M 5/16809
                                                                417/413.1
2008/0294094 A1   11/2008 Mhatre et al.
(Continued)

FOREIGN PATENT DOCUMENTS

EP          3124066 A1      2/2017

OTHER PUBLICATIONS

Int'l Search Report and Written Opinion dated Sep. 18, 2018 in Int'l Application No. PCT/US2018/035107.
(Continued)

*Primary Examiner* — Laura A Bouchelle
(74) *Attorney, Agent, or Firm* — BakerHostetler (57) ABSTRACT

An electronic injector including a needle insertion assembly configured to move a needle in an insertion direction from a first needle position where the needle is above the surface of a patient's skin to a second needle position where the needle pierces the patient's skin. The injector further includes a member mechanically coupled to the needle and configured to move when the needle. The injector further includes an optical detector having a generally planar detection surface and configured to detect movement of the member based on a change in a transverse projection of the member onto the detection surface and output a signal based on the change in the transverse projection. Additional, a processor is configured to determine the position of the needle based on the output signal, and the transverse projection of the member changes when the needle moves.

12 Claims, 7 Drawing Sheets

(52) U.S. Cl.
CPC ............ *A61M 2005/14252* (2013.01); *A61M 2205/3306* (2013.01)

(56) References Cited

U.S. PATENT DOCUMENTS

| | | |
|---|---|---|
| 2014/0194854 A1 | 7/2014 | Tsals |
| 2016/0228644 A1* | 8/2016 | Cabiri ................ A61M 5/3204 |
| 2019/0015582 A1* | 1/2019 | Naftalovitz ....... A61M 5/14248 |

OTHER PUBLICATIONS

Office Action dated Apr. 7, 2020 in Chinese Application No. 201880036318.1.

* cited by examiner

VERTICAL ASSEMBLY OF PCB

CROSS-REFERENCE TO RELATED APPLICATIONS

This application is a section 371 of International Application No. PCT/US2018/035107, filed May 30, 2018, which was published on Dec. 6, 2018 under International Publication No. WO 2018/222697 A1, and which claims priority to U.S. Provisional Patent Application No. 62/512,496, filed on May 30, 2017, the disclosure of each of which is incorporated herein by reference in its entirety.

BACKGROUND OF THE INVENTION

The present invention is directed to a printed circuit board (PCB). More specifically, the present invention is directed to a PCB mounted vertically inside an electronic patch injector.

For patients who wear electronic patch injectors, it is desirable for the injectors to be as inconspicuous as possible. This has led to an industry trend in minimizing the aspect ratio of the device to make it flat and low profile. Consequently, conventional designs of electronic patch injectors have maximized the size of the PCB within the device by taking advantage of the largest planar dimension within its housing, for example, the PCB has typically been oriented parallel to the contact surface of the skin.

In some existing devices where the PCB is parallel to the contact surface of the skin, the following conditions exist: 1) a cutout in the PCB is necessary to provide an aperture for the needle, 2) most (if not all) of the components within the device need to be mounted on the PCB, 3) the PCB occupies unnecessary space, adding to the footprint of the device, and 4) it is difficult to sense the vertical movement of the needle.

Typically, with the PCB oriented parallel to the surface of the skin, a respective optical position sensor is positioned directly beneath a reflective arm (or flag) of a needle assembly and/or a needle shield assembly. The optical sensor emits light beam vertically (perpendicular to the surface of the PCB) and the arm reflects a portion of the emitted light back to a detector in the optical sensor. The position of the needle and/or shield is then calculated based on the intensity of the detected light. Small changes in the position of the needle or shield result in even smaller changes in the intensity of the detected light. Thus, it is difficult to accurately detect the position of the needle.

Applicant has improved the accuracy of the needle and/or needle shield position detection by mounting an optical position sensor perpendicular to the motion of the respective component. In some exemplary embodiments, one or more optical position sensors are mounted on a vertically oriented PCB (i.e., perpendicular to the skin contact surface). Additionally, by mounting the PCB in a vertical orientation, the footprint of the PCB may be reduced, minimizing the size of the device and providing more flexibility in the design layout for the components within the device. Moreover, mounting the PCB vertically may also allow the electronic components within the device to be easily removed from the housing for recycling without having to remove some or all of the bio-contaminated components.

BRIEF SUMMARY OF THE INVENTION

In an exemplary embodiment of the present invention, an electronic injector is disclosed. The electronic injector may include a needle insertion assembly configured to move a needle in an insertion direction from a first needle position where the needle is above the surface of a patient's skin to a second needle position where the needle pierces the patient's skin, a needle shield moveable from a first needle shield position where the needle is at least partially covered to a second needle shield position where the needle is exposed, at least one member mechanically coupled to either the needle or the needle shield and configured to move when the respective needle or needle shield moves, at least one optical detector having a generally planar detection surface and configured to detect movement of the at least one member based on a change in a transverse projection of the at least one member onto the detection surface and output a signal based on the change in the transverse projection, and a processor configured to determine the position of the respective needle or needle shield based on the output signal. The transverse projection of the at least one member may change when the respective needle or needle shield moves.

In some embodiments of the electronic injector the at least one optical detector is mounted on a planar surface of a printed circuit board, the surface defined by the two largest dimensions of the printed circuit board, and the planar surface is oriented perpendicular to the surface of the patient's skin when the needle is in the second needle position.

In some embodiments of the electronic injector the processor is mounted on the printed circuit board.

In some embodiments of the electronic injector, the at least one optical sensor is configured to output the signal in proportion to the change in the transverse projection of the at least one member onto the detection surface.

In some embodiments of the electronic injector, the at least one member is positioned at an elevation distance away from the at least one optical detector and the elevation distance remains constant during movement of the respective needle or needle shield.

In some embodiments of the electronic injector, the at least one member includes a needle member configured to move when the needle moves and a needle shield member configured to move when the needle shield moves; the at least one optical detector includes a needle optical detector having a generally planar detection surface and configured to detect movement of the needle member based on a change in a transverse projection of the needle member onto the detection surface and output a signal based on the change in the transverse projection, a needle shield optical detector having a generally planar detection surface and configured to detect movement of the needle shield member based on a change in a transverse projection of the needle shield member onto the detection surface and output a signal based on the change in the transverse projection; the processor configured to determine the position of the needle based on the output signal from the needle optical sensor and the position of the needle shield based on the output signal from the needle shield optical sensor; and the transverse projection of the needle member changes when the needle moves and the transverse projection of the needle shield member changes when the needle shield moves.

BRIEF DESCRIPTION OF THE SEVERAL VIEWS OF THE DRAWINGS

The foregoing summary, as well as the following detailed description of preferred embodiments of the invention, will be better understood when read in conjunction with the appended drawings. For the purpose of illustrating the invention, the drawings show embodiments which are presently preferred. It should be understood, however, that the invention is not limited to the precise arrangements and instrumentalities shown.

In the drawings.

DETAILED DESCRIPTION OF THE INVENTION

Reference will now be made in detail to embodiments of the invention, examples of which are illustrated in the accompanying drawings. The terminology used in the description of the invention herein is for the purpose of describing particular embodiments only and is not intended to be limiting of the invention.

The following description is directed towards various embodiments of an electronic patch injector in accordance with the present invention.

Referring to the drawings in detail, where like numerals indicate like elements throughout, there is shown in FIGS. 1-10B embodiments of a flexible collar.

Figure 1:
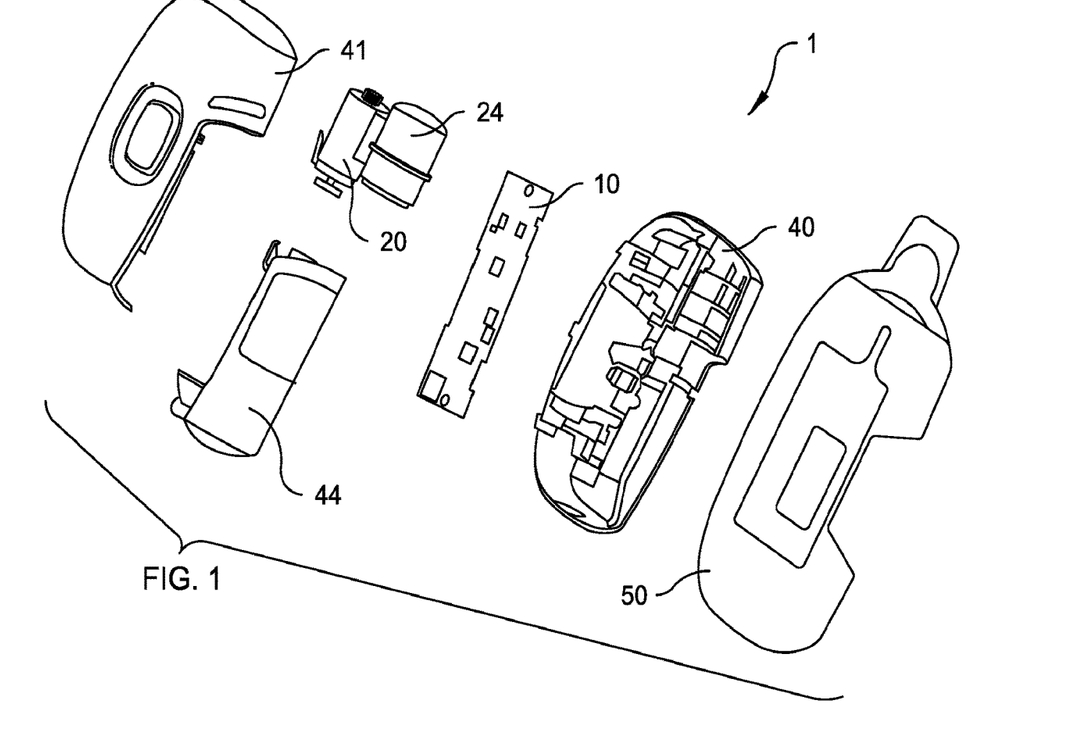
FIG. 1 is an exploded view illustrating an exemplary embodiment of an electronic patch injector.

FIG. 1 illustrates an electronic patch injector 1 according to an exemplary embodiment of the present invention. The electronic patch injector 1 may include a lower housing 40 and an upper housing 41 collectively for housing internal components, such as PCB 10, which is discussed in more detail in the description that follows. The lower and upper housing 40, 41 may also include a door 44 for inserting a medicinal vial (not shown). The bottom surface of the lower housing 41 may have an adhesive pad assembly 50 attached thereto for removably attaching the electronic patch injector 1 to a skin surface of a patient (once attached, this surface is hereafter referred to as a contact surface).

Figure 2:
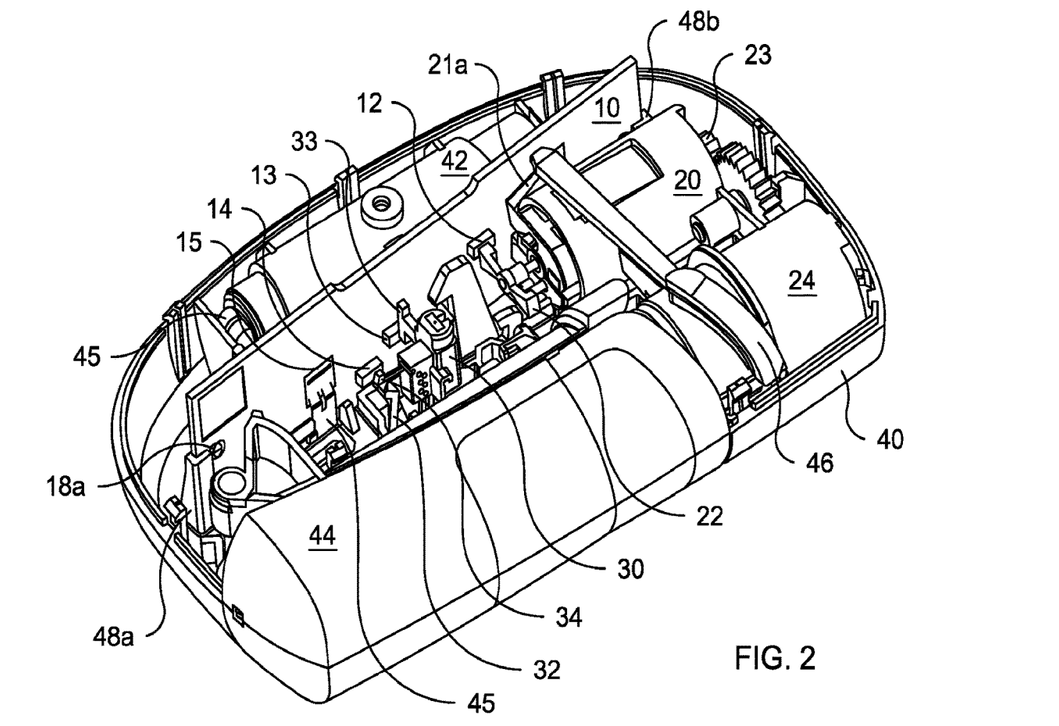
FIG. 2 is a top, front, right-side perspective view illustrating the electronic patch injector shown in FIG. 1 with a top housing hidden from view.
Figure 3:
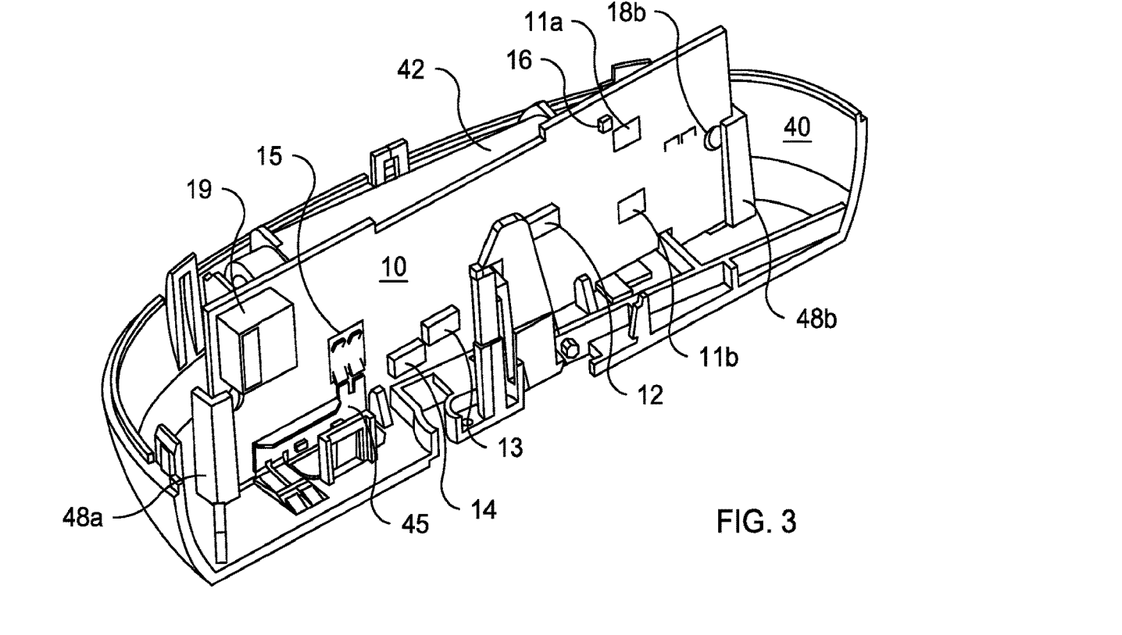
FIG. 3 is a top, front, right-side perspective, cross-sectional view illustrating the electronic patch injector shown in FIG. 1.
Figure 4:
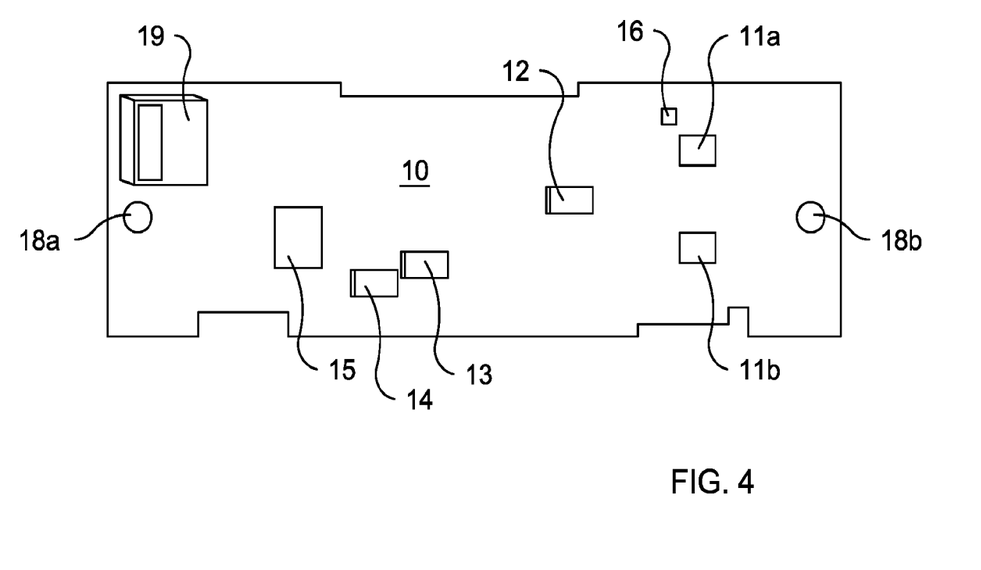
FIG. 4 is a top, front, right-side perspective view illustrating a PCB from the electronic patch injector shown in FIG. 1.
Figure 5:
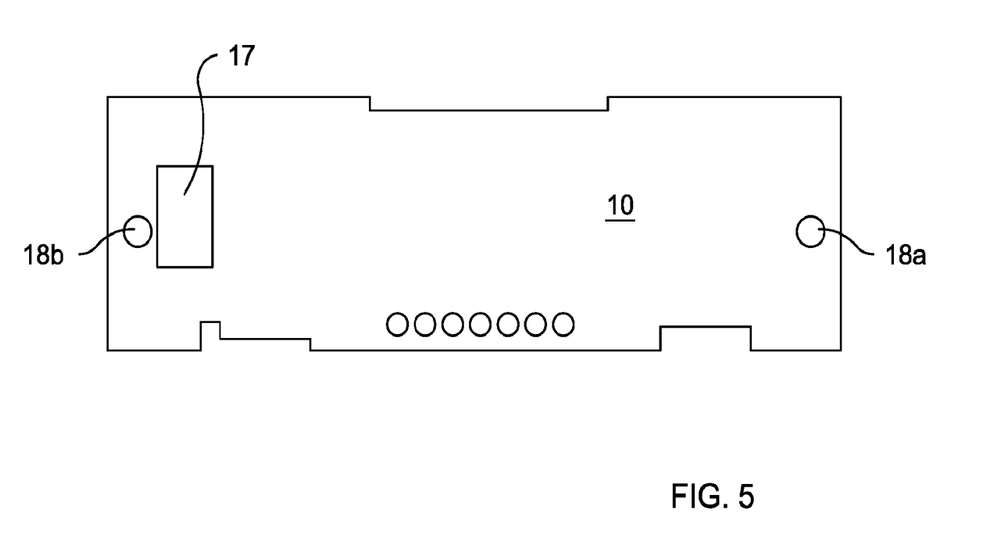
FIG. 5 is a top, back, left-side perspective view illustrating the PCB from the electronic patch injector shown in FIG. 1.

FIG. 2 depicts the internal components of the electronic patch injector 1. The PCB 10 may be positioned vertically or substantially vertically to the adhesive pad assembly 50. Thus, once attached to the skin surface, the PCB may be oriented vertically to the contact surface. The PCB 10 may be positioned to separate the some components within the device from the power supply components, such as a battery 42 for supplying electrical power to the PCB 10 and other components either directly through the PCB 10 or directly to the other components. The side of the PCB 10 that faces the battery 42 will be referred to herein as the power side, and the side of the PCB that faces the other components will be referred to herein as the component side. As shown in FIG. 7, a terminal of the battery 42 is in electrical communication with the PCB 10 through a first spring clip 47 (see FIG. 6) which makes electrical connection with a first power pad 17 (FIG. 5) on the power side of the PCB 10. The first spring clip 47 uses a mechanical spring force to maintain electrical communication with the battery 42 and the PCB 10 without the need for a solder connection. However, in other embodiments not shown, the first spring clip 47 may be soldered to the battery 42 and/or the first power pad 17. The first spring clip 47 is removably positioned on a protrusion 43 extending vertically from the lower housing 40. The other terminal of the battery 42 is also in electrical communication with the PCB 10 through a second spring clip 45 which makes electrical connection with a second power pad 15 on the component side of the PCB 10. The second spring clip 45 is routed through a gap under the PCB to the opposite side and uses a mechanical spring force to maintain electrical communication with the battery 42 and the PCB 10 without the need for a solder connection. However, in other embodiments not shown, the second spring clip 45 may be soldered to the battery 42 and/or the second power pad 15.

The PCB 10 may be held in place by first, second, third, and fourth PCB support members 48a, 49a, 48b, 49b, which are integral with a lower surface of the lower housing 40 and spaced away from the sides of the lower and upper housings 40, 41. The first and third PCB support members 48a, 48b have right-angle support surfaces, one surface of which abuts the component side of the PCB 10 and a second surface abuts a vertical edge of the PCB 10. The second and fourth PCB support members 49a, 49b face the power side of the PCB 10 and have a pin that extends perpendicular toward corresponding holes 18a, 18b of the PCB 10. In the assembled orientation shown in FIGS. 2 and 7, the pins of the second and fourth PCB support members 49a, 49b engage the holes 18a, 18b respectively to secure the PCB against the first and third PCB support members 48a, 48b respectively. The PCB 10 may be removably assembled into the patch injector 1 by slightly flexing the PCB 10 and/or the second and fourth PCB support members 49a, 49b until the pins of the second and fourth PCB support members 49a, 49b engage the respective holes 18a, 18b of the PCB 10. The holes 18a, 18b and the first, second, third, and fourth PCB support members are positioned to hold the PCB 10 elevated from the lower surface of the lower housing 40. In other words, there is a gap between the lower edge of the PCB 10 and the lower housing 40. When the upper housing 41 is assembled to the lower housing 40, there is also a gap between the PCB 10 and the upper housing 41. Thus, each of the edges of the PCB 10 is isolated from the external walls of the lower and upper housing 40, 41. This may help isolate the PCB 10 from flexural stress that may be applied to the housing 41 and may isolate the PCB from internal and external vibrations transmitted through the lower and upper housing 40, 41.

The patch injector may also include a motor 20 configured to drive a telescopic screw assembly 24 through a plurality of gears 23 for dispensing medicament (not shown) out of the vial. The motor 20 may be electrically connected to the PCB 10 via a first motor spring clip 21a and a second motor spring clip (not shown). The first and second motor spring clips 21a may be soldered to the motor 20, but are held with a mechanical spring force against first and second motor power pads 11a, 11b (FIGS. 3 and 4) on the PCB 10 to be in electrical communication with the PCB 10. The motor spring clips 21a permit the PCB 10 to be removably installed without the need for a solder connection to the PCB 10. Moreover, the motor spring clips 21a may help dampen vibrations from the motor to the PCB 10 and thus reduce the vibrations to the lower and upper housings 40, 41. The motor 20 may also include an encoder 22 extending from a shaft opposite from the gear 23. The encoder 22 may be configured to rotate about an axis parallel with surface of the component side of the PCB 10 in front of a motor position detector 12 mounted on the PCB 10. Thus, movement of the motor 20 causes one or more arms of the encoder 22 to rotate toward and away from the motor position detector 12. The motor position detector 12 may be configured to output a signal based on the detected position of the encoder 22.

The patch injector 1 may also include needle insertion assembly 30 for translating a needle 31 (FIGS. 8A-8C) through an opening in the lower housing 40 and through the contact surface. For example, the needle insertion is configured to move the needle 31 in an insertion direction from a first needle position where the needle 31 is above the surface of the patient's skin to a second needle position where the needle pierces the patient's skin. The needle insertion assembly 30 also includes a needle member 33 (FIG. 2) mechanically coupled to the needle 31 and configured to move when the needle 31 moves. The needle member 33 is positioned near a needle optical detector 13 for detecting movement of the needle member 33 and ultimately for detecting movement of the needle 31. The needle optical detector 13 may have a generally planar detection surface which may be parallel to component side of the PCB 10. In the exemplary embodiment shown in FIG. 2, the needle member 33 is configured to translate in the same direction as the needle 31, and thus, move toward and away from the needle optical detector 13 by passing in front of the needle optical detector 13. The needle optical detector 13 may be configured to output a signal based on the detected position of the needle member 33.

The patch injector 1 may also include a needle shield assembly 32, which is configured to pivot from a first needle shield position where the needle 31 is at least partially covered to a second needle shield position where the needle 31 is exposed. The needle shield assembly 32 also includes a needle shield member 34 mechanically coupled to the needle shield assembly 32 and configured to move when the needle shield assembly 32 moves. The needle shield member 34 is positioned near a needle shield optical detector 14 for detecting movement of the needle shield member 34. The needle shield optical detector 14 may have a generally planar detection surface which may be parallel to component side of the PCB 10. In the exemplary embodiment shown in FIG. 2, the needle member 33 is configured to rotate about an axis perpendicular with the surface of the component side of the PCB 10 and move toward and away from the needle shield optical detector 14 by passing in front of the needle shield optical detector 14. For example, the needle shield member 34 rotates in a plane parallel to the detection surface of the optical needle shield detector 14 at an elevation distance away from it. The needle shield optical detector 14 may be configured to output a signal based on the detected position of the needle shield member 34.

Figure 6:
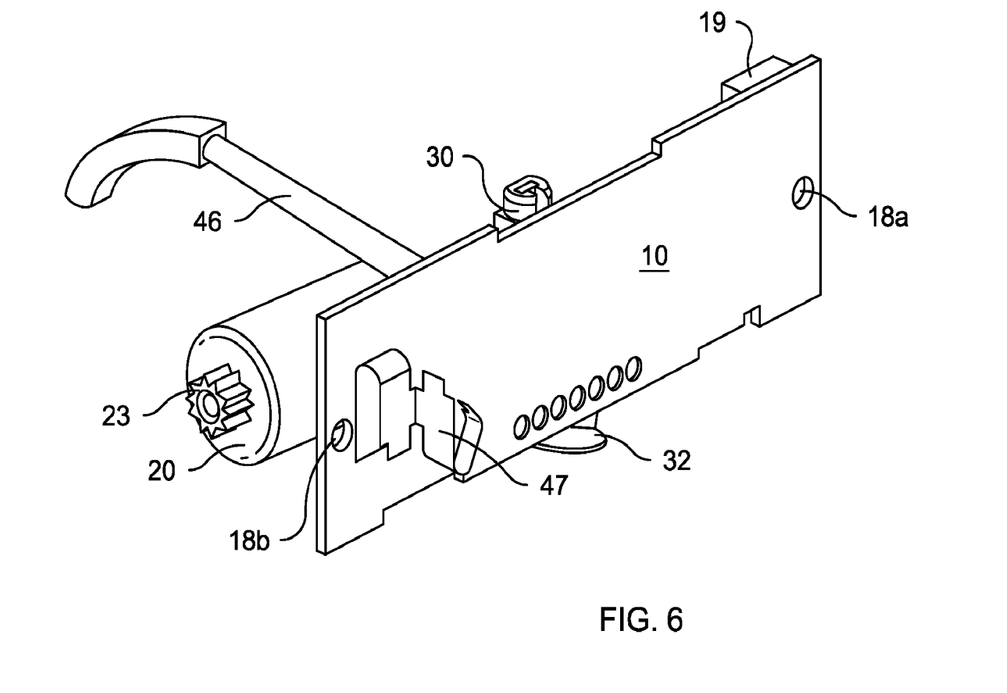
FIG. 6 is a top, back, left-side perspective view illustrating some of the internal components from the electronic patch injector shown in FIG. 1.
Figure 7:
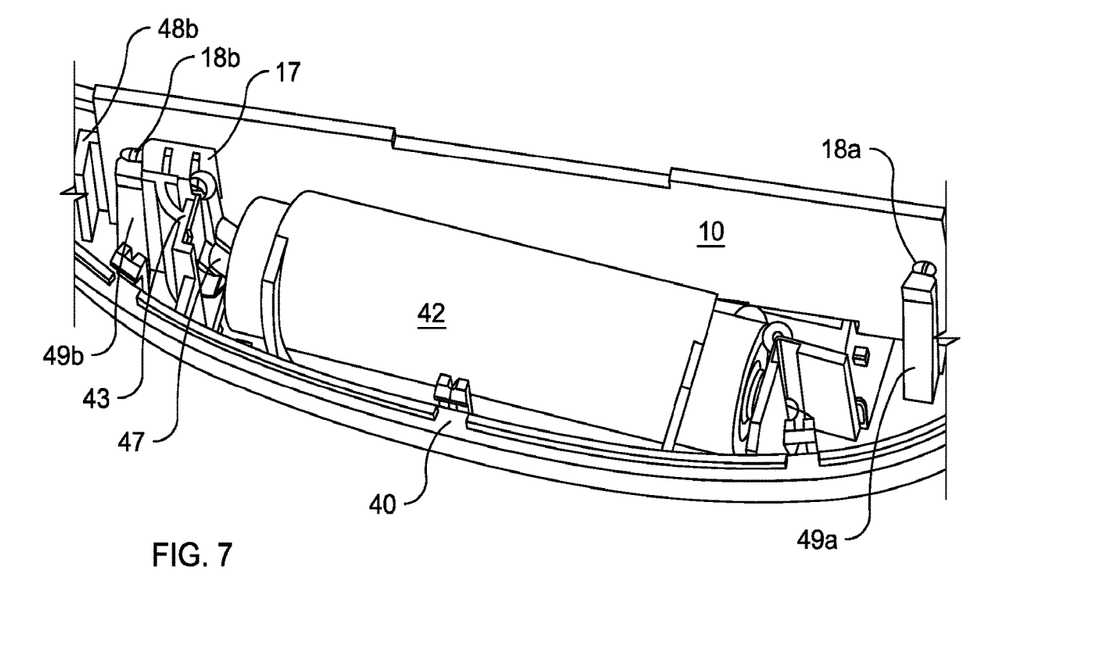
FIG. 7 is a top, back, left-side perspective view illustrating some of the internal components from the electronic patch injector shown in FIG. 1.

As shown in FIGS. 2 and 6, the patch injector also includes a light guide 46. One end of the light guide 46 may be positioned within a window in the upper housing 41 and a second end may be positioned near a light source 16 (FIG. 3) mounted on the PCB 10, such as an LED. The light guide 46 is configured to guide light from the light source 16 to the outside of the patch injector 1 to visually communicate information to the patient.

The PCB 10 may also include a processor 19. The processor 19 may be a single circuit component or may include several circuit components which work in conjunction with the processor 19. The processor may be configured to determine the position of the needle 31, needle shield 32, and motor 22 based on the output signals from the respective needle optical detector 13, needle shield optical detector 14, and motor position detector 12.

Figure 9A:
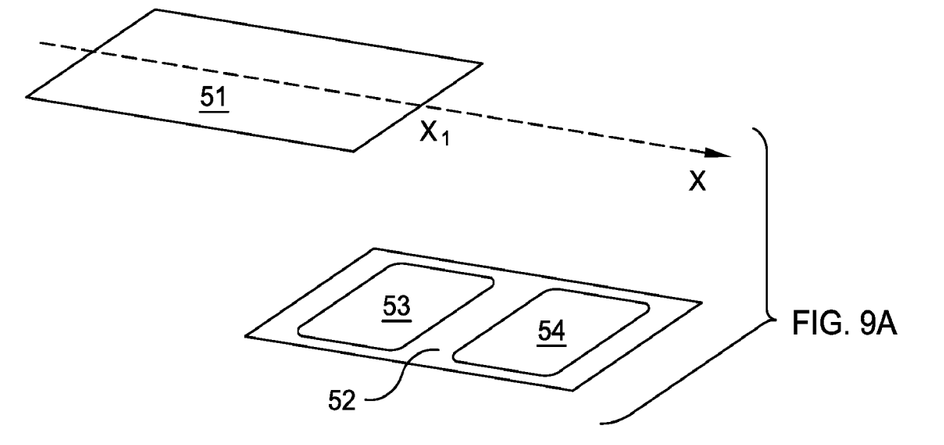
FIGS. 9A and 9B are conceptual perspective views demonstrating position detection of a lateral moving object by an exemplary optical sensor.
Figure 9B:
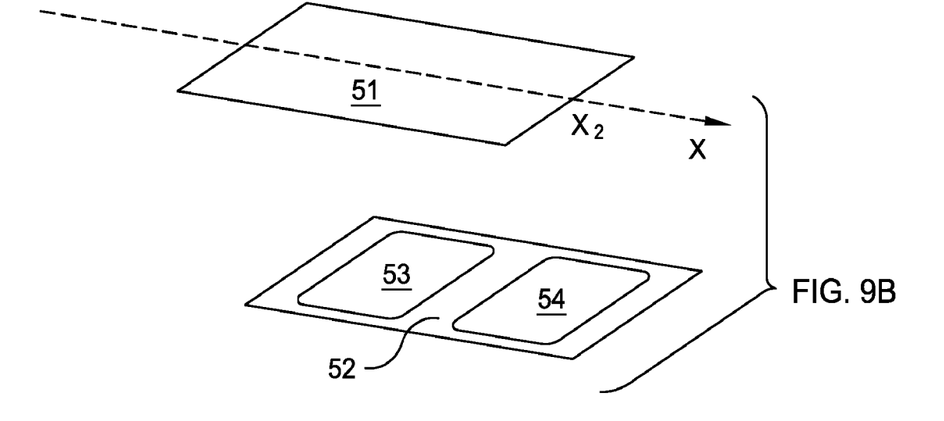
Figure 9C:
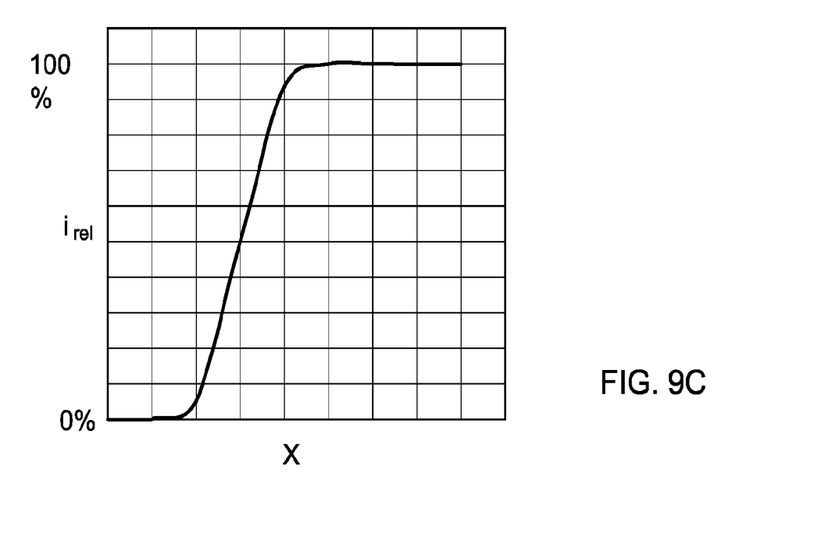
FIG. 9C is a graphical representation of the relative current output of the optical position sensor shown in FIGS. 9A and 9B.

FIGS. 9A-10B illustrate an exemplary operation of an optical detector 52, such as, for example, a Vishay Semiconductors VCNT2020. Each of the needle optical detector 13, the needle shield optical detector 14, and the motor position detector 12 may be comprised of the optical detector 52. The optical detector 52 may have a generally planar detection surface which is opposite from a mounting surface. The detection surface may include an emitter 53 configured to emit light, such as infrared light, and a collector 54, configured to receive the light emitted from the emitter 53 and output current based on the intensity of the light received. FIGS. 9A-9B illustrates a reflective body 51 passing in front of the optical detector 52 as it is translated in the X-direction. The reflective body 51 may be, for example, a reflective surface on the encoder 22, needle member 33, or needle shield member 34. In FIG. 9A, the reflective surface is positioned at $X_1$ and the transverse projection of the reflective body is shown in shade partially covering the emitter 53. FIG. 9B shows the reflective body 51 after it has been translated to position $X_2$, where its transverse projection completely covers the emitter 53 and partially covers the collector 54. FIG. 9C plots the current output as the reflective body 51 is translated in the X-direction from a position where its transverse projection does not cover any portion of the optical detector 52, through $X_1$ and $X_2$, and to a position where its transverse projection completely covers the emitter 51 and collector 53. As can be seen in FIG. 9C, the output current as a function of position in the X-direction is represented as an S-curve. Further, a portion of the S-curve may be approximated linearly such that the position in the X-direction can be approximated as being proportional to the output current. Although not shown, the optical detector 52 has a similar output current versus position profile when the reflective body 51 is translated in a Y-direction laying in the same plane as the X-direction, but perpendicular thereto. Thus, any linear movement of the reflective body 51 within a plane parallel to the optical detector 52 may be linearly approximated by the output current.

Figure 10A:
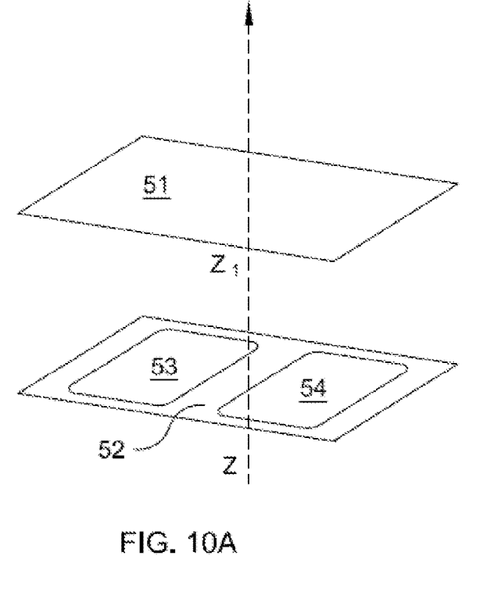
FIGS. 10A and 10B are conceptual perspective views demonstrating position detection of a vertical moving object by the optical sensor shown in FIGS. 9A and 9B.
Figure 10B:
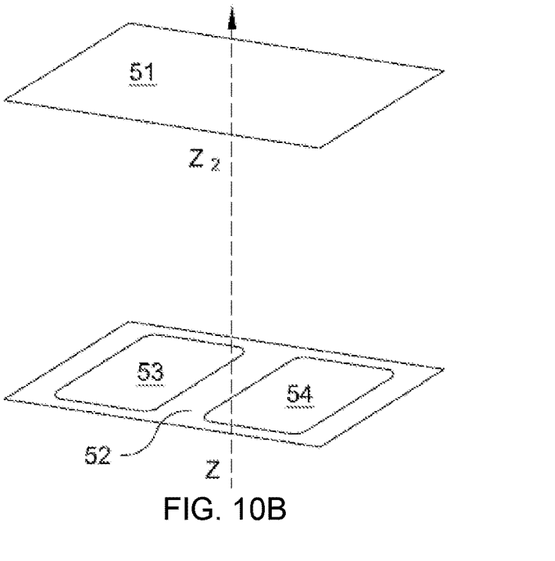
Figure 10C:
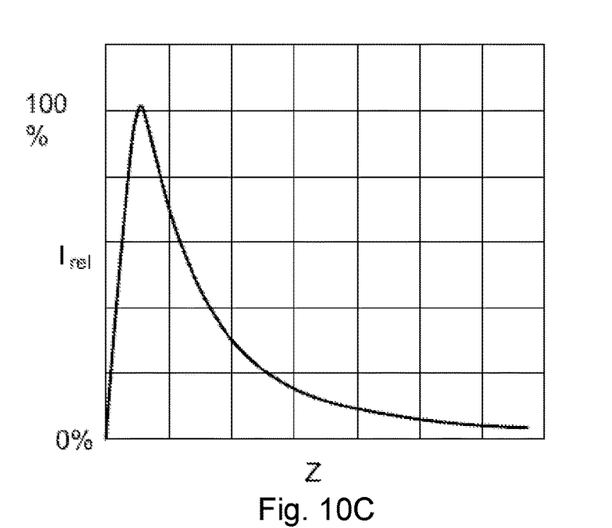
FIG. 10C is a graphical representation of the relative current output of the optical position sensor shown in FIGS. 10A and 10B.

FIG. 10A illustrates an exemplary operation of the optical detector 52 as a reflective body 51 is moved in a Z-direction perpendicular to optical detector 52. For example, the transverse projection of body 51 is shown completely covering the emitter 53 and the collector 54 at the positions $Z_1$ and $Z_2$. FIG. 10B plots the current output as the reflective body 51 is translated in the Z-direction from a position where it contacts the optical detector 52, through $Z_1$ and $Z_2$, and to a position beyond $Z_2$. As can be seen in FIG. 10B, the output current as a function of position in the Z-direction has a maximum value at some position in the Z-direction and decays exponentially as the distance in the Z-direction increases from this point.

Figure 8A:
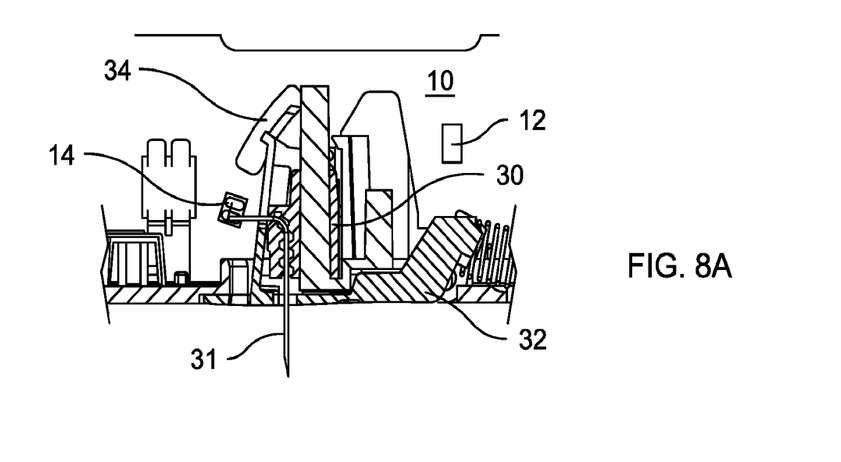
FIGS. 8A-8C are right-side perspective views illustrating a needle insertion assembly in various configurations.
Figure 8B:
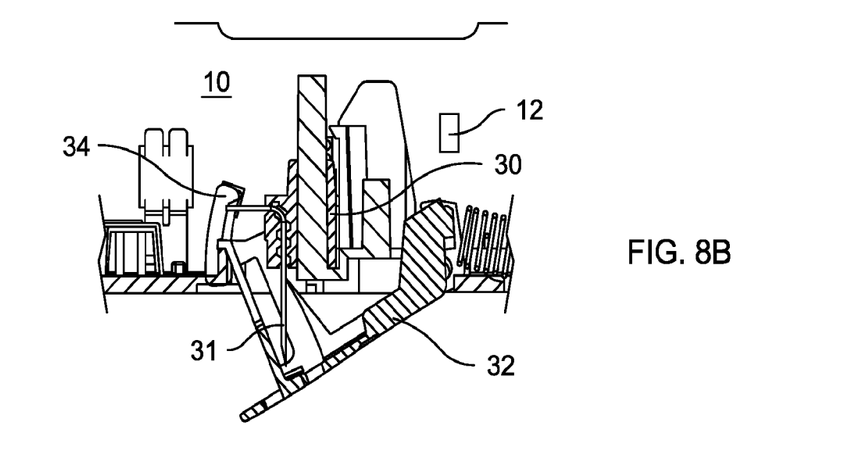
Figure 8C:
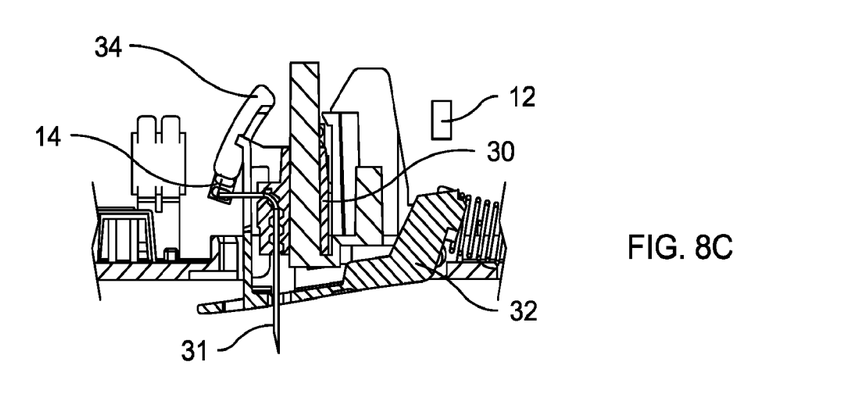

Turning to FIGS. 8A-8C, the operation of the needle shield assembly 32 is shown. FIG. 8B shows a configuration where the needle shield assembly 32 is covering the needle 31. In this configuration, the needle shield member 32 is also covering the needle shield optical detector 14. For example, the transverse projection of the needle shield member 32 onto the needle shield optical detector 14 is at a first position. As the needle shield assembly 32 pivots toward the lower housing 40 (FIG. 8C), the needle shield member 34 rotates away from the needle shield optical detector 14. For example, the transverse projection of the needle shield member 32 onto the needle shield optical detector 14 moves to a second position. As the needle shield assembly 32 pivots further toward the lower housing 40 into a closed position (FIG. 8A), the needle shield member 34 rotates further away from the needle shield optical detector 14. For example, the transverse projection of the needle shield member 32 is no longer on the needle shield optical detector 14 (however, in some embodiments, the needle shield member may still transversely project onto the needle shield optical sensor). Because the relationship between position and the output signal of the needle shield position detector 14 can be linearly approximated, the angular position of the needle shield member 34 can be linearly correlated to the angular position of the needle shield assembly 32. Although the needle member 33 is not shown in FIGS. 8A-9C, the transverse projection of the needle member 33 onto the needle optical detector 13 may behave in substantially the same way as the needle shield member 34. For example, as the needle 31 moves in the insertion direction, the needle member 33 also moves in the same direction. As the needle member moves, a transverse projection thereof moves across the needle optical detector 13. Because the relationship between position and the output signal of the needle detector 13 and can be linearly approximated, the linear position of the needle member 33 can be linearly correlated to the linear position of the needle 31. Thus, the position of the needle 31 and the needle shield assembly 32 can be calculated based on the output signals from the needle optical detector 13 and the needle shield optical detector 14, respectively.

The foregoing detailed description of the invention has been disclosed with reference to specific embodiments. However, the disclosure is not intended to be exhaustive or to limit the invention to the precise forms disclosed. Those skilled in the art will appreciate that changes could be made to the embodiments described above without departing from the broad inventive concept thereof. Therefore, the disclosure is intended to cover modifications within the spirit and scope of the present invention as defined by the appended claims.

We claim:

1. An electronic injector comprising:
    a housing having a base defining a base aperture,
    a needle extending along an insertion direction and configured to extend through the base aperture and pierce a patient's skin,
    a needle shield defining an aperture, wherein the needle is configured to selectively extend through the aperture, wherein the needle shield is moveable from a first needle shield position where the needle is at least partially covered and the aperture is misaligned with the needle along the insertion direction to a second needle shield position where the needle is exposed and the aperture is aligned with the needle along the insertion direction,
    a member mechanically coupled to the needle and configured to move when the needle moves,
    a battery,
    a printed circuit board having a planar surface defined by the two largest dimensions of the printed circuit board, wherein the planar surface is oriented perpendicular to the base, the planar surface defining a first side and an opposing second side and the printed circuit board being positioned within the housing to separate the battery from the needle, the needle shield and the member, the battery being electrically connected with the first side of the planar surface,
    an optical detector mounted to the second side of the planar surface and configured to detect movement of the member and output a signal based on the movement of the member, and
    a processor configured to determine the position of the needle based on the output signal.

2. The electronic injector according to claim 1, wherein the processor is mounted on the printed circuit board.

3. The electronic injector according to claim 1, wherein the optical detector is configured to output the signal in proportion to a change in a position of the member.

4. The electronic injector according to claim 1, wherein the member is positioned at an elevation distance away from the optical detector and the elevation distance remains constant during movement of the needle.

5. The electronic injector according to claim 1, further comprising:
    a needle shield member mechanically coupled to the needle shield and configured to move when the needle shield moves;
    a needle shield optical detector having a generally planar detection surface and configured to detect movement of the needle shield member based on the movement of the needle shield member and output a signal based on the movement of the needle shield member; and
    the processor configured to determine the position of the needle shield based on the signal from the needle shield optical detector.

6. The electronic injector according to claim 1, wherein the needle shield is configured to rotate about an axis angularly offset from the insertion direction to move from the first needle shield position to the second needle shield position.

7. An electronic injector comprising:
    a housing having a base defining a base aperture;
    a needle extending along an insertion direction and configured to extend through the base aperture and pierce a patient's skin,
    a needle shield defining an aperture, wherein the needle is configured to selectively extend through the aperture, wherein the needle shield is moveable from a first needle shield position where the needle is at least partially covered to a second needle shield position where the needle is exposed,
    a needle shield member mechanically coupled to the needle shield and configured to move when the needle shield moves,
    a battery,
    a printed circuit board having a planar surface defined by the two largest dimensions of the printed circuit board, wherein the planar surface is oriented perpendicular to the base, the planar surface defining a first side and an opposing second side and the printed circuit board being positioned within the housing to separate the battery from the needle, the needle shield and the member, the battery being electrically connected with the first side of the planar surface, an optical detector mounted to the second side of the planar surface and configured to detect movement of the needle shield member and output a signal based on the movement of the needle shield member, and a processor configured to determine the position of the needle shield based on the output signal.

8. The electronic injector according to claim 7, wherein the processor is mounted on the printed circuit board.

9. The electronic injector according to claim 7, wherein the optical detector is configured to output the signal in proportion to a change in a position of the needle shield member.

10. The electronic injector according to claim 7, wherein the needle shield member is positioned at an elevation distance away from the optical detector and the elevation distance remains constant during movement of the needle shield.

11. The electronic injector according to claim 7, wherein the needle shield assembly is configured about an axis angularly offset from the insertion direction to move from the first needle shield position to the second needle shield position.

12. The electronic injector according to claim 7, wherein the aperture is misaligned with the needle along the insertion direction when the needle shield is in the first needle shield position and the aperture is aligned with the needle along the insertion direction when the needle shield is in the second needle shield position.

* * * * *